United States Patent [19]
Misra

[11] Patent Number: 5,612,323
[45] Date of Patent: Mar. 18, 1997

[54] PHOSPHINIC ESTER SUBSTITUTED BENZOPYRAN DERIVATIVES

[75] Inventor: Raj N. Misra, Hopewell, N.J.

[73] Assignee: Bristol-Myers Squibb Company, Princeton, N.J.

[21] Appl. No.: 479,324

[22] Filed: Jun. 7, 1995

[51] Int. Cl.⁶ .............................. A61K 31/665; C07F 9/28
[52] U.S. Cl. ............................................ 514/100; 549/220
[58] Field of Search ........................... 546/22; 549/218, 549/220; 514/89, 100

[56] References Cited

U.S. PATENT DOCUMENTS

| | | | |
|---|---|---|---|
| 3,330,838 | 7/1967 | Augstein et al. | 260/309.6 |
| 3,812,157 | 5/1974 | Lin et al. | 260/345.2 |
| 3,953,506 | 4/1976 | Spicer et al. | 260/553 |
| 4,238,501 | 12/1980 | Kabbe et al. | 424/283 |
| 4,251,537 | 2/1981 | Evans | 424/267 |
| 4,363,811 | 12/1982 | Evans et al. | 424/267 |
| 4,366,163 | 12/1982 | Evans et al. | 424/267 |
| 4,391,815 | 7/1983 | Evans | 424/274 |
| 4,428,881 | 1/1984 | Hedrich et al. | 548/491 |
| 4,481,213 | 11/1984 | Evans | 424/283 |
| 4,568,692 | 2/1986 | Evans | 514/456 |
| 4,571,406 | 2/1986 | Evans et al. | 514/456 |
| 4,575,511 | 3/1986 | Evans et al. | 514/456 |
| 4,602,022 | 7/1986 | Cozzi et al. | 514/337 |
| 4,659,737 | 4/1987 | Kabbe et al. | 514/456 |
| 4,687,779 | 8/1987 | Evans | 514/456 |
| 4,734,421 | 3/1988 | Hammond et al. | 514/274 |
| 4,772,603 | 9/1988 | Evans | 514/241 |
| 4,782,083 | 11/1988 | Cassidy et al. | 514/456 |
| 4,831,050 | 5/1989 | Cassidy et al. | 514/422 |
| 4,904,784 | 2/1990 | Evans et al. | 546/90 |
| 4,925,839 | 5/1990 | Quagliato et al. | 514/212 |
| 4,943,582 | 7/1990 | Evans et al. | 514/320 |
| 4,971,982 | 11/1990 | Attwood et al. | 514/337 |
| 4,988,723 | 1/1991 | Shiokawa et al. | 514/392 |
| 5,006,523 | 4/1991 | Atwal | 514/227.5 |
| 5,011,837 | 4/1991 | Atwal et al. | 514/227.8 |
| 5,013,853 | 5/1991 | Gericke et al. | 549/401 |
| 5,021,432 | 6/1991 | Yamanaka et al. | 514/337 |
| 5,028,711 | 7/1991 | Stenzel et al. | 546/196 |
| 5,053,427 | 10/1991 | Stemp et al. | 514/456 |
| 5,061,813 | 10/1991 | Atwal | 549/399 |
| 5,071,871 | 12/1991 | Blarer et al. | 514/456 |
| 5,082,858 | 1/1992 | Garcia et al. | 514/456 |
| 5,095,016 | 3/1992 | Ohtuka et al. | 514/233.5 |
| 5,096,914 | 3/1992 | Stenzel et al. | 514/392 |
| 5,104,890 | 4/1992 | Shiokawa et al. | 514/370 |
| 5,140,031 | 8/1992 | Atwal et al. | 514/302 |
| 5,143,924 | 9/1992 | Gericke et al. | 514/337 |
| 5,143,936 | 9/1992 | Yamanaka et al. | 514/456 |
| 5,145,985 | 9/1992 | Timar et al. | 548/525 |
| 5,210,234 | 5/1993 | Evans et al. | 549/398 |
| 5,238,937 | 8/1993 | Gericke et al. | 514/253 |
| 5,254,555 | 10/1993 | Stemp et al. | 514/256 |
| 5,268,386 | 12/1993 | Harada et al. | 514/456 |
| 5,276,168 | 1/1994 | Atwal | 549/404 |
| 5,278,169 | 1/1994 | Atwal | 514/302 |
| 5,286,753 | 2/1994 | Schaus et al. | 514/657 |
| 5,310,750 | 5/1994 | Berge et al. | 514/402 |
| 5,310,932 | 5/1994 | Atwal et al. | 548/454 |
| 5,317,029 | 5/1994 | Inazu et al. | 514/422 |
| 5,318,969 | 6/1994 | Yamanaka et al. | 514/247 |
| 5,374,643 | 12/1994 | Atwal et al. | 514/364 |
| 5,393,771 | 2/1995 | Atwal | 514/394 |
| 5,401,848 | 3/1995 | Atwal | 546/153 |

FOREIGN PATENT DOCUMENTS

| | | |
|---|---|---|
| 0076075 | 4/1983 | European Pat. Off. . |
| 0091748 | 10/1983 | European Pat. Off. . |
| 0093535 | 11/1983 | European Pat. Off. . |
| 0120427 | 10/1984 | European Pat. Off. . |
| 0126311 | 11/1984 | European Pat. Off. . |
| 0139992 | 5/1985 | European Pat. Off. . |
| 0205292 | 12/1986 | European Pat. Off. . |
| 0214818 | 3/1987 | European Pat. Off. . |
| 0247266 | 12/1987 | European Pat. Off. . |
| 0250077 | 12/1987 | European Pat. Off. . |
| 0274821 | 7/1988 | European Pat. Off. . |
| 0287196 | 10/1988 | European Pat. Off. . |
| 0339562 | 11/1989 | European Pat. Off. . |

(List continued on next page.)

OTHER PUBLICATIONS

A.P. Terent'ev et al., "Optically Active Isocyanates. III. Synthesis and Spectropolarimetric Study of Optically Active N–derivative of Urea", *Chemical Abstracts*, vol. 71, Abstract No. 69992h, p. 250 (1969).

J. Bermudez et al., "5–Hydroxytryptamine (5–HT₃) Receptor Antagonists. 2. 1-Indolinecarboxamides", *J. Med. Chem.*, vol. 33, pp. 1929–1932 (1990).

P.D. Leeson et al., "4–Amido–2–carboxytetrahydroquinolines, Structure–activity Relationships for Antagonism at the Glycine Site of the NMDA Receptor", *J. Med. Chem.*, vol. 35, pp. 1954–1968 (1992).

J.L. Hughes et al., "Cardiovascular Activity of Aromatic Guanidine Compounds", *J. Med. Chem.*, vol. 18, No. 11, pp. 1077–1088 (1975).

M. Mazza et al., "N–Acilindoline Ad Attivita Fitotossica", *Farmaco. Ed. Sci.*, vol. 31, No. 10, pp. 746–754 (1976).

T. Sekiya et al., "Benzene–condensed Cyclic Amine β–amino Carboxamides as Antichycardiacs and Vasodilators", *Chemical Abstracts*, vol. 113, p. 694 (1990).

(List continued on next page.)

Primary Examiner—Amelia Owens
Attorney, Agent, or Firm—Ellen K. Park

[57] ABSTRACT

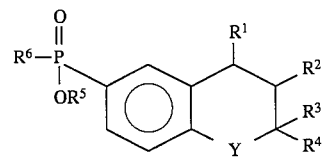

and pharmaceutically acceptable salts thereof wherein Y is a single bond, $-CH_2-$, $-C(O)-$, $-S-$ or $-N(R^{11})-$; and $R^1$ to $R^6$ are as defined herein. These compounds have potassium channel activating activity and are useful, therefore for example, as cardiovascular agents.

5 Claims, No Drawings

FOREIGN PATENT DOCUMENTS

| | | |
|---|---|---|
| 0344747 | 12/1989 | European Pat. Off. . |
| 0350805 | 1/1990 | European Pat. Off. . |
| 0351767 | 1/1990 | European Pat. Off. . |
| 0359537 | 3/1990 | European Pat. Off. . |
| 0377966 | 7/1990 | European Pat. Off. . |
| 0377967 | 7/1990 | European Pat. Off. . |
| 0385584 | 9/1990 | European Pat. Off. . |
| 0389861 | 10/1990 | European Pat. Off. . |
| 0401010 | 12/1990 | European Pat. Off. . |
| 0402716 | 12/1990 | European Pat. Off. . |
| 0407200 | 1/1991 | European Pat. Off. . |
| 0412531 | 2/1991 | European Pat. Off. . |
| 0431741 | 6/1991 | European Pat. Off. . |
| 0462761 | 12/1991 | European Pat. Off. . |
| 0488616 | 6/1992 | European Pat. Off. . |
| 0525768 | 2/1993 | European Pat. Off. . |
| 2801187 | 7/1978 | Germany . |
| 2204868 | 11/1988 | United Kingdom . |
| WO8707607 | 12/1987 | WIPO . |
| WO89/09217 | 10/1989 | WIPO . |
| WO91/09031 | 6/1991 | WIPO . |
| WO92/05174 | 4/1992 | WIPO . |
| WO92/14733 | 9/1992 | WIPO . |
| WO92/22293 | 12/1992 | WIPO . |

OTHER PUBLICATIONS

R. Albrecht et al., "Chemotherapeutic Nitroheterocycles. XI (1). Indanylamides and Indanylesters of 5–nitrofurancarboxylic Acids and Analogous Compounds as Antimicrobial Agents", *Chimie Therapeutique*, vol. 7, No. 1, pp. 9–13 (1972).

H.J. Petersen et al., "Synthesis and Hypotensive Activity of N–Alkyl–N–cyano–N'–pyridylguanidines", *J. of Med. Chem.*, vol. 21, No. 8, pp. 773–781 (1978).

V.A. Ashwood et al., "Synthesis and Antihypertensive Activity of 4–(Cyclic amido)–2H–1–benzopyrans", *J. Med. Chem.*, 29, pp. 2194–2201 (1986).

C.R. Rasmussen et al., "Improved Procedures for the Preparation of Cycloalky–Arylalkyl–, and Arylthioureas", *Synthesis*, pp. 456–459 (1988).

V.V. Mozolis et al., "Preparation of N–Substituted Thiourea", *Russian Chem. Reviews*, 42(7), pp. 587–595 (1973).

J.M. Evans et al., "Synthesis and Antihypertensive Activity of Substituted trans–4–Amino–3,4–dihydro–2,2–dimethyl–2H–1–benzopyran–3–ols", *J. Med. Chem.*, 26, pp. 1582–1589 (1983).

R.W. Lang et al., "Synthesis of Selectively Trifluoromethylated Pyridine Derivatives as Potential Antihypertensives", *Helvetica Chimica Acta*, vol. 72, pp. 596–601 (1988).

P. Sebok et al., "Selective synthesis of Analogues of the Natural Precocenes, Synthesis and Regioselective (–Alkylation of 6–Chloro–and 6–Tert–Butyl–7,8–Dihyedroxy–2,2–Dimethyl–4–Chromanones", *Heterocycles*, 27, pp. 2595–2607 (1988).

P. Teixidor et al., "Improved Preparation of Precocene II, Unexpected Results in the Reduction of Alkoxy Substituted Acetophenones and 4–Chromanones with Sodium Borohydride", *Heterocycles*, 27, pp. 2459–2465 (1988).

A. Banerji et al., "Enolates of O–Hydroxyacetophenones: Novel Synthesis of 2,2–Dialkyl–4–Chromanones", *Tetrahedron Letters*, No. 38, pp. 2685–2686 (1979).

G. Ariamala et al., "A Simple Route for the Synthesis of 4–Chlorochromanes and Chroman–4–one", *Tetrahedron Letters*, 29, No. 28, pp. 3487–3488 (1988).

PHOSPHINIC ESTER SUBSTITUTED BENZOPYRAN DERIVATIVES

BRIEF DESCRIPTION OF THE INVENTION

In accordance with the present invention novel compounds having potassium channel activating activity which are useful, for example, as cardiovascular agents, are disclosed. These compounds have the general formula

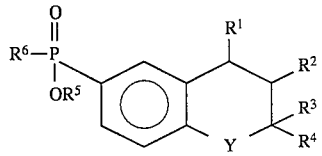

where $R^1$ is

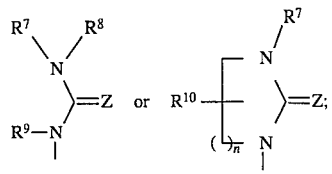

$R^2$ is hydrogen, hydroxy, or —OC(O)$R^{11}$;

$R^3$ and $R^4$ are each independently hydrogen, alkyl or arylalkyl; or $R^3$ and $R^4$ taken together with the carbon atom to which they are attached form a 3- to 7-membered carbocyclic ring;

$R^5$ is hydrogen, alkyl or aryl;

$R^6$ is alkyl, aryl or arylalkyl;

$R^7$ is aryl, arylalkyl, heterocyclo or (heterocyclo)alkyl;

$R^8$ is hydrogen or alkyl;

or $R^7$ and $R^8$ taken together with the atoms to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl; the so-formed groups may optionally be substituted with alkyl, alkoxy, alkylthio, halogen or trifluoromethyl and may further include an aryl group fused to 2 carbon atoms of such so-formed group;

$R^9$ and $R^{10}$ are independently hydrogen, alkyl, alkenyl, aryl, arylalkyl, cycloalkyl or cycloalkylalkyl; or $R^{10}$ can be an aryl group fused to 2 carbon atoms of the cyanoguanidine ring portion;

$R^{11}$ is hydrogen, alkyl, haloalkyl, aryl, arylalkyl, cycloalkyl or (cycloalkyl)alkyl;

Y is a single bond, —CH$_2$—, —C(O)—, —O—, —S— or —N($R^{11}$)—;

Z is NCN, S or O; and n is an integer of 1 to 3.

The compounds of this invention possess antiischemic activity and are useful, for example as cardiovascular agents.

DETAILED DESCRIPTION OF THE INVENTION

The invention relates to the phosphinic ester compounds of formula I above, to compositions and the methods of using such compounds. The compounds of formula I are useful, for example, as cardiovascular agents.

Listed below are definitions of various terms used to describe the compounds of the instant invention. These definitions apply to the terms as they are used throughout the specifications (unless they are otherwise limited in specific instances either individually or as part of a larger group).

The term "alkyl" refers to both straight and branched chain groups having 1 to 8 carbon atoms preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups optionally substituted with one or more substituents selected from halogen, alkoxy, aryl, alkylaryl, haloaryl, cycloalkyl, (cycloalkyl)alkyl, hydroxy, alkylamino, alkyl-substituted amino, alkanoylamino, arylcarbonylamino, nitro, cyano, thiol or alkylthio.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups having at least 2 carbon atoms further containing at least one carbon to carbon double bond.

The term "alkynyl" refers to any of the above alkyl groups having at least 2 carbon atoms further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl or 2-naphthyl; phenyl, 1-naphthyl or 2-naphthyl, mono-substituted with (C$_1$-C$_4$)-alkyl, (C$_1$-C$_4$)-alkylthio, (C$_1$-C$_4$)-alkoxy, halo, nitro, cyano, hydroxy, amino, (alkyl)amino, alkyl-substituted amino, —NH—(C$_1$-C$_4$)-alkyl, —N((C$_1$-C$_4$)-alkyl), heterocyclo, —CF$_3$, —OCHF$_2$,

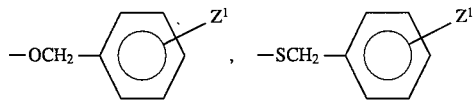

(where $Z^1$ is hydrogen, (C$_1$-C$_4$)-alkyl, (C$_1$-C$_4$)-alkylthio, (C$_1$-C$_4$)-alkoxy, halo, hydroxy or —CF$_3$), —O—CH$_2$-cycloalkyl, or —S—CH$_2$-cycloalkyl; or phenyl, 1-naphthyl or 2-naphthyl, di-substituted with methyl, methoxy, methylthio, halo, —CF$_3$, nitro, amino, —OCHF$_2$, carboxylic acid or carboxylic ester. The term "aryl" also includes those groups listed above fused to a five- or six-membered ring which optionally contains an O, S or N atom (the nitrogen atom being substituted by an $R^7$ group). Preferred aryl groups include unsubstituted phenyl and monosubstituted phenyl wherein the substituents are (C$_1$-C$_4$)-alkyl, methoxy, halo, nitro, cyano or —CF$_3$.

The term "heterocyclo" or "hetero" refers to fully saturated or unsaturated rings of 5 to 7 atoms containing one or two oxygen and/or sulfur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl, imidazolyl, thiazole, oxazole, pyrazole, isoxazole and isothiazole. The term "hetero" also includes bicyclic tings wherein the five- or six-membered ting containing oxygen and/or sulfur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term "heterocyclo" or "hetero" also includes such monocyclic and bicyclic rings wherein an available carbon atom is substituted with a $(C_1-C_4)$-alkyl, aryl, $(C_1-C_4)$-alkylthio, $(C_1-C_4)$-alkoxy, halo, nitro, keto, cyano, hydroxy, azo, thiazo, amino, —NH—$(C_1-C_4)$-alkyl, —N($(C_1-C_4)$-alkyl$)_2$, —$CF_3$, (aminoester)alkyl, carboxylic acid, carboxylic ester, —$OCHF_2$ or $(C_1-C_4)$-alkoxy further substituted with a carboxylic acid or such monocyclic and bicyclic rings wherein two or three available carbons have substituents selected from methyl, methoxy, methylthio, halo, —$CF_3$, nitro, hydroxy, amino and —$OCHF_2$.

The term "substituted amino" refers to a group of the formula —$NZ^2Z^3$ wherein $Z^2$ is hydrogen, alkyl, cycloalkyl, aryl, arylalkyl, (cycloalkyl)alkyl, morpholinylalkyl, heterocyclo or (heterocyclo)alkyl and $Z^3$ is hydrogen, alkyl, cycloalkyl, aryl, arylalkyl, haloalkyl, hydroxyalkyl, alkoxyalkyl, thioalkyl, (cycloalkyl)alkyl or hydroxyalkyl further substituted with a carboxylic ester or carboxylic acid, with the proviso that when $Z^2$ is hydrogen, then $Z^3$ is other than hydrogen; or $Z^2$ and $Z^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl; or 1-pyrrolidinyl, 1-piperidinyl, 1-azepinyl substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as $(C_1-C_4)$-alkyl- or aryl-sulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents or at the phosphorous atom. Consequently, compounds of formula I can exist in diastereomeric forms or in mixtures thereof. The below described processes can utilize racemates, enantiomers or diastereomers as starting materials. When diastereomeric products are prepared, they can be separated by conventional methods for example, chromatographic or fractional crystallization. Preferred compounds are those with the 3R or 4S stereochemistry on the benzopyran.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Compounds of formula

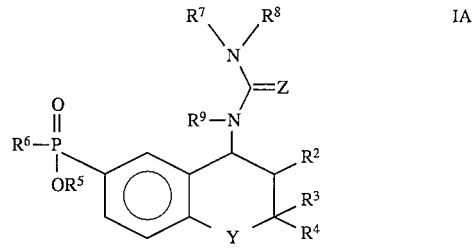

IA i.e. compounds of formula I where $R^1$ is

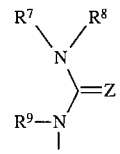

are prepared by treatment of a thiourea of the formula

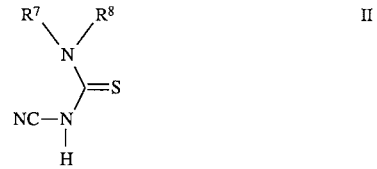

II with an amine of the formula

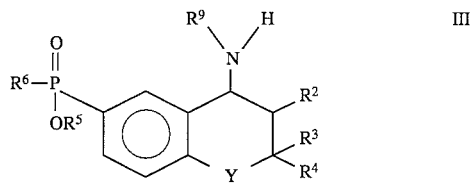

III in the presence of a coupling agent, such as a carbodiimide, in a solvent, such as dimethylformamide, tetrahydrofuran, acetonitrile or dichloromethane. Preferably, the carbodiimide is of the formula $$\begin{array}{c} R^a \\ \phantom{R^a}\diagdown \\ \phantom{R^aR^a}N-CH_2-(CH_2)_m-N=C=N-R^c.HX' \\ \phantom{R^a}\diagup \\ R^b \end{array} \quad IV$$

wherein X' is halogen, $R^a$, $R^b$ and $R^c$ are independently alkyl, cycloalkyl, phenyl, phenylalkyl, cycloalkylalkyl or $R^a$ and $R^b$ together with the nitrogen atom to which they are attached form 1-pyrrolidinyl, 1-piperidinyl, 4-morpholinyl, 4-thiamorpholinyl, 4-alkyl-1-piperazinyl or 4-phenylalkyl-1-piperazinyl. Most preferably the carbodiimide of formula IV is 1-(3-dimethylaminopropyl)-3-ethylcarbodiimide hydrochloride.

The compounds formula IA can also be prepared by converting a compound of formula III by standard methods (i.e., the Rasmussen and Mozolis references cited above) to a thiourea of the formula

V

Subsequent heating with monosodium cyanamide in the presence of a carbodiimide such as 1-(3-dimethylaminopropyl)-3-ethylcarbodiimide or dicyclohexylcarbodiimide in an organic solvent produces the compounds of formula IA.

The compounds of formula IA can also be prepared by reacting an amine of formula III with diphenylcyanocarbonimidate to produce a compound of the formula

VI

Reaction of a compound of formula VI with an amine of the formula $$R^7R^8NH \quad VII$$

in a polar solvent such as isopropanol produces the compounds of formula IA.

Compounds of the formula IA where Z is oxygen or sulfur can be prepared by reacting an amine of the formula III with $$\begin{array}{c} Z \phantom{xx} R^7 \\ \| \phantom{xx} \diagup \\ L^*-C-N \\ \phantom{L^*-C-N}\diagdown \\ \phantom{L^*-C-N}R^8 \end{array} \quad VIII$$

where L* is a leaving or activating groups in an organic solvent such as dimethylformamide, tetrahydrofuran, acetonitrile or dichloromethane. Suitable leaving or activating groups include chlorine or 4-nitrophenyloxy.

Compounds of formula IA where $R^8$ is hydrogen and Z is oxygen or sulfur can be made by reacting amine III with a compound of formula $$R^7N=C=Z. \quad IX$$

The thiourea of formula II, wherein $R^8$ is hydrogen can be prepared by heating an isothiocyanate of the formula $$R^7N=C=S \quad X$$

with either monosodium cyanamide or with cyanamide in the presence of an organic base, such as triethylamine.

The other thioureas of formula II can be prepared by standard methods described in the literature, such as by C. R. Rasmussen et al., *Synthesis*, p. 456 (1988), and V. V. Mozolis et al., *Russian Chemical Reviews*, 42, p. 587 (1973).

The amino alcohol of formula III where $R^2$ is hydroxyl can be prepared from 4-hydroxybromo-benzene or preferably from 4-hydroxyiodobenzene by methods described in the literature such as *Tetrahedron Letter*, 35, p. 6405–6408 (1994), to form the bromides or iodides of formula

XI where Y is oxygen. Treatment of the bromides or preferably iodides of formula XI with phosphinic acid esters of formula $$\begin{array}{c} O \\ \| \\ R^6-P-H \\ | \\ OR^5 \end{array} \quad XII$$

under an inert atmosphere and dry conditions in the presence of a palladium(O) catalyst, such as tetrakis(triphenylphosphine)palladium and an organic base, such as triethylamine in an organic solvent such as tetrahydrofuran, dimethylformamide or perferably acetonitrile at a temperature of 20° C. to 150° C. produces phosphinic add esters of formula

XIII

Epoxidation of the olefins of formula XIII with commercial bleach or m-peroxylchlorobenzoic acid in the presence of a chiral manganese catalyst of formula

XIV as described by N. H. Lee, et al., *Tetrahedron Letters*, 1991, 32, p. 5055–5058, produces the epoxides of formula

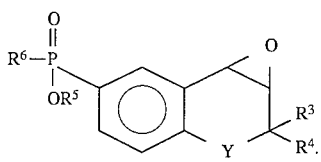  XV

Either stereoisomer of epoxide XV can be prepared depending on the chirality of catalyst XIV or diastereomeric mixtures of formula XV can be obtained by treatment with m-peroxylchlorobenzoic acid in an organic solvent such as dichloromethane. Subsequent treatment of the epoxide of formula XV with an amine of formula

R$^9$NH$_2$     XVI or aqueous ammonium hydroxide in an organic solvent such as tetrahydrofuran or ethanol produces the amino alcohol of formula III, where R$^2$ is hydroxyl.

Compounds of formula III where R$^2$ is hydrogen, can be prepared from compounds of formula XIII by a sequence of steps which involve (a) catalytic hydrogenation (b) radical bromination and (c) displacement of bromide with an amine of formula XVI.

All other compounds of formula III can be prepared by methods described in the literature such as those by C. Almansa et al., *J. Med. Chem.*, 36, 2121 (1993), (Y=—C(O)—); V. A. Ashwood et al., 34, 3261 (1991), (Y=NR$^{11}$); and D. G. Smith et al., EP-0322251 (Y=S).

The phosphinic acid esters XII can be prepared by the coupling of phospinic acids of formula

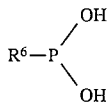   XVII with an alcohol (R$^5$OH) in the presence of a carbodiimide reagent and amine catalyst such as 4-dimethylaminopyridine in an inert solvent such as tetrahydrofuran or dimethylformamide.

Compounds of formula XV wherein Y is a single bond can be prepared according to D. R. Buckle, et al., *J. Med. Chem.*, 34, 919(1991).

Compounds of formula XV wherein Y is CH$_2$ can be prepared by methods described in V. A. Ashwood, et al., *J. Med. Chem.*, 34, 3261 (1991).

The compounds of the formula IA wherein R$^8$ and/or R$^9$ is hydrogen, can exist as a mixture of tautomers represented by the following structures. The tautomeric products are obtained in relative mounts that differ from compound to compound. All forms are included in the scope of formula I.

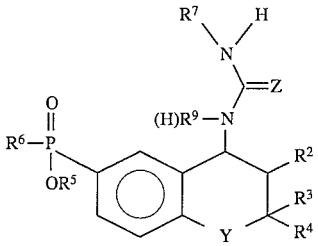  I'

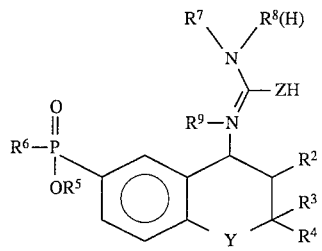  I"

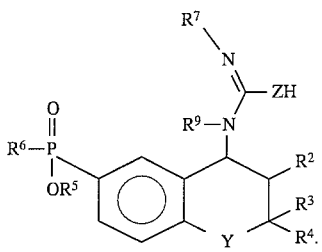  I'''

Preparation of Compounds of Formula IB

The compounds of formula

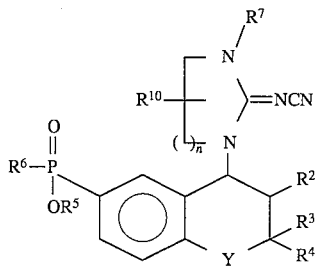  IB i.e. compounds of the formula I wherein R$^1$ is

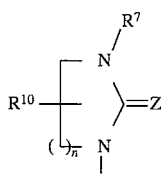

can be prepared by treating a diamine of the formula

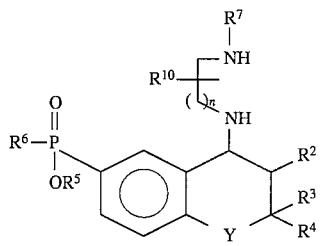  XVIII with dimethyl-N-cyanodithioiminocarbonate to form compounds of the formula

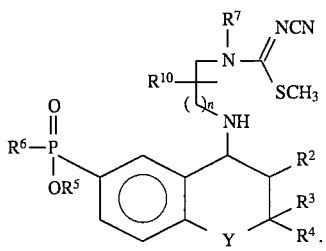

Subsequent treatment with mercuric acetate in an alcoholic solvent such as methanol produces the compounds of formula IB.

The compounds of formula IB can also be prepared by treating a diamine of formula XVIII with diphenylcyanocarbonimidate in an alcoholic solvent, such as 2-propanol.

The compounds of formula IB wherein $R^2$ is —OCOR$^{11}$ can be prepared by acylation of the alcohols of formula IB, (where $R^2$ is hydroxy), with an acid chloride of the formula

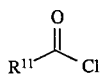

in the presence of a base catalyst, such as pyridine, 4-dimethylaminopyridine or triethylamine.

The compounds of formula XVIII wherein $R^2$ is trans hydroxyl are obtained by treatment of an epoxide of formula XV with a diamine of the formula

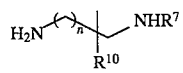

in an alcoholic solvent, such as ethanol.

Compounds of formula XVIII can also be prepared from the amine III and an alkylating agent of the formula

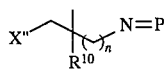

wherein P is a protecting group such as phthalimide and X" is a leaving group, such as Cl, Br or I, in the presence of a base catalyst, such as triethylamine followed by deprotection.

All other compounds of formula I may be prepared by modification of the procedures discussed herein as known by those skilled in the art. The intermediates used to prepare compounds of formula I are described herein or may be derived from known compounds by those skilled in the art or are commercially available.

The compounds of the present invention can have asymmetric centers at carbons 2–4 of the benzopyran ring. Also, any one of the R's can have an asymmetric carbon. In addition, the phosporous atom may be asymmetric. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

If any of the R substituents, X or Y groups contain reactive groups such as hydroxy or amino that can interfere with the epoxide opening reaction or any other reactions, they should be protected with appropriate protecting groups.

Compounds of formula I have been found to be "selective antiischemic agents". The term "selective antiischemic agents" means that these compounds possess little or no vasodilator activity (i.e., these compounds have IC$_{50}$ (rat aorta) values greater than that of the known potassium channel activator, cromakalim). Therefore, in the treatment of ischemic hearts, the compounds of the instant invention are less likely to cause coronary steal, profound hypotension and coronary under-perfusion.

The preferred compounds of the present invention are those compounds of formula I where Y is oxygen;

Z is oxygen or NCN;

$R^1$ is

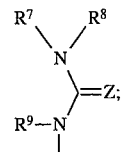

$R^2$ is hydroxyl;

$R^3$ and $R^4$ are methyl groups;

$R^7$ is aryl; and $R^8$ and $R^9$ are hydrogens.

Compounds of formula I may be used as antiischemic agents, i.e., for the treatment of ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of the compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatment of male impotence, as well as for the promotion of hair growth (e.g., in the treatment of male pattern baldness), and as anti-asthmatic agents.

The compounds of this invention can also be formulated in combination with a diuretic such as chlorothiazide, hydrochlorothiazide, flumethiazide, hydroflumethiazide, bendroflumethiazide, methylchlothiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

(3S-trans)-[4-[[[(4-Chlorophenyl)amino](cyanoimino)methyl]-amino]-3,4-dihydro-3-hydroxy-2,2-dimethyl-2H-1-benzopyran-6-yl]phenylphosphinic acid, methyl ester

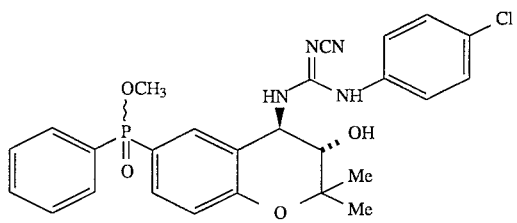

A. Phenylphosphinic acid, methyl ester

To a solution of phenylphosphinic acid (5.00 g, 35.2 mmol), anhydrous methanol (7.0 mL, 170 mmol) and 4-dimethylaminopyridine (425 mg, 3.48 mmol) in 50 mL of THF (distilled from ketyl) was added EDAC (8.05 g, 42 mmol) at room temperature. The reaction was stirred for 24 hours then partitioned between HCl solution (75 mL of 1M aq) and ethyl acetate (75 mL). The organic layer was separated, washed with HCl solution (75 mL of 1M aq), sodium bicarbonate solution (75 mL of 5% aq) then dried (sodium sulfate) and concentrated in vacuo to afford the crude title compound as a colorless liquid (1.24 g, 7.95 mmol, 23%).

B. 3-Chloro-3-methyl-1-butyne

Into a 22 L 3-necked, round-bottom flask equipped with a nitrogen inlet, a 1L addition funnel, and a mechanical stirrer, was added calcium chloride (2.4 Kg, MW 111, 21.6 mol, 1 eq), hydroquinone (22 g), and concentrated hydrochloric acid (8.8L, 12M, 108 mol, 5 eq). The solution was cooled to 10° C. with an ice-water bath, then the alcohol (1.82 Kg, 21.6 mol.) added through the addition funnel over 15 minutes while maintaining the reaction temperature below 25° C. The reaction was stirred gently for one hour at 20° C. (the temperature was maintained below 25° C. by adding more ice to the water bath as necessary). The reaction turned from colorless to yellow to dark green. The biphasic mixture was then separated in two 6L separatory funnels. The dark green top layer was drained into a 3L 1-necked round-bottomed flask and magnetically stirred with 500 g of milled potassium carbonate. The crude mixture was distilled under reduced pressure. The following fractions were collected:

| Fraction | Head temp. | Vacuum | Amount | Impurity Levels |
| --- | --- | --- | --- | --- |
| 1 | 35–38° C. | 138–147 mbar | 150 g | 4% |
| 2 | 38–42° C. | 138–147 mbar | 1000 g | 8% |
| 3 | 42–45° C. | 60–90 mbar | 190 g | 50% |

Fractions 1 and 2 were deemed acceptable by NMR analysis and were combined (1.15 kg, 52% yield uncorrected) for use in the next reaction.

Fraction 3 was discarded. $^1$H-NMR (300 MHz, CDCl$_3$): δ 2.6 (s, 1H), 1.8 (s, 6H). $^{13}$C-NMR (300 MHz, CDCl$_3$): δ 34.7, 56.9, 72.2, 86.6.

C. 1-[(1,1-Dimethyl-2-propynyl)oxy]-4-iodobenzene

To a solution of 4-iodophenol (6.05 g, 27.5 mmol), in anhydrous acetonitrile (25 mL) cooled to 0° C. was added 1,8-diazabicyclo[5.4.0]undec-7-ene (DBU, 4.50 mL, 30.1 mmol). The solution was stirred for 10 minutes then the title B compound (2.56 g, 25 mmol) was added followed by copper(II) chloride dihydrate (5.1 mg, 0.030 mmol). The reaction mixture was stirred at 0° C. for five hours then concentrated in vacuo. The residue was partitioned between 200 mL of toluene and 40 mL of 1M aq HCl solution. The organic layer was washed with two-40 mL portions of 1M aq HCl solution, two-40 mL portions of 1M aq NaOH solution, brine then dried (magnesium sulfate) and concentrated in vacuo to give a pale yellow liquid. The crude material was purified by bulb-to-bulb distillation (100° C., 0.1 mm) to afford the title compound as a colorless liquid (5.65 g, 19.7 mmol, 79%).

D. 6-Iodo-2,2-dimethyl-2H-1-benzopyran

A solution of the title C compound (5.00 g, 17.5 mmol) in 5 mL of diethylaniline was heated under argon to 180° for 2.5 hours. The resulting dark solution was cooled to room temperature then partitioned between 50 mL of 1M aq HCl solution and 50 mL of ether. The organic layer was separated, washed with 50 mL of 1M aq HCl solution, 50 mL of 5% aq sodium thiosulfate solution then dried (magnesium sulfate) and concentrated in vacuo to give a yellow oil. The crude material was purified by flash chromatography (Merck silica, 15×5.0 cm, 1:19 ethyl acetate/hexane) to afford the title compound as a yellow oil (4.90 g, 17.1 mmol, 98%).

E. (2,2-Dimethyl-2H-1-benzopyran-6-yl)phenylphosphinic acid, methyl ester

A solution of the title A compound (2.40 g, 15.4 mmol), aryl iodide (the title D compound; 2.39 g, 8.36 mmol), 4-methylmorpholine (929 mg, 9.20 mmol) in 25 mL of anhydrous acetonitrile was sparged with argon for 10 minutes. To the resulting solution was added at room temperature tetrakistriphenylphosphine palladium (485 mg, 0.42 mmol). The resulting heterogeneous reaction mixture was heated to 80° C. to give a homogeneous yellow solution. The reaction mixture was stirred for 45 minutes then the resulting red solution was cooled to room temperature and concentrated in vacuo. The residue was partitioned between 50 mL of ethyl acetate and 50 mL of 1M aq HCl solution. The aqueous layer was separated and extracted with 25 mL of ethyl acetate. The organic extracts were combined, washed with 50 mL of 5% aq sodium thiosulfate solution. The aqueous layer was extracted with 25 mL of ethyl acetate. The combined organic extracts were dried (magnesium sulfate) and concentrated in vacuo to give a dark oil. The crude oil was purified by flash chromatography (Merck silica, 24×5.0 cm, 4:1 ethyl acetate/hexane) to afford the title compound as a pale yellow oil (2.18 g, 6.94 mmol, 83%).

F. (1aS-cis)-(1a,7b-Dihydro-2,2-dimethyl-2H-oxireno[c][1]benzopyran-6-yl)phenylphosphinic acid, methyl ester To a solution of the title E compound (2.17 g, 6.91 mmol) in 14 mL of methylene chloride was added (S,S)-(+)-N,N'-bis(3,5-di-t-butylsali-cylidene)-1,2-cyclohexanediamino-manganese(III) chloride (88 mg, 0.14 mmol) and 4-phenylpyridine-N-oxide (44 mg, 0.14 mmol) at room temperature. The mixture was stirred for five minutes then added to a freshly prepared cooled (0° C.) solution of 48 mL of Clorox bleach and 16 mL of 0.05M aq $Na_2HPO_4$ (pH adjusted to 11.3 by addition of 1M aq NaOH). The resulting two phase mixture was stirred rapidly at 0° C. for one hour then transferred to a separatory funnel and extracted with two-30 mL portions of methylene chloride. The organic extracts were combined washed with 50 mL of brine, dried (sodium sulfate), filtered and concentrated in vacuo to give a dark oil. The crude material was purified by flash chromatography (Merck silica, 24×5.0 cm, ethyl acetate) to afford the title compound as a yellow-brown oil (1.19 g, 5.79 mmol, 79%).

G. (3S-trans)-(4-Amino-3,4-dihydro-3-hydroxy-2,2-dimethyl-2H-1-benzopyran-6-yl)phenylphosphinic acid, methyl ester To a solution of the title F compound (1.90 g, 5.76 mmol) in 7.5 mL of ethanol was added 7.5 mL of 30% aq ammonium hydroxide solution at room temperature. The reaction mixture was stirred for 48 hours then partitioned between 40 mL of ether and 40 mL of brine. The aqueous layer was separated and extracted with an additional 40 mL of ether. The organic extracts were combined, dried (sodium sulfate) and concentrated in vacuo to afford the crude title compound as a pale yellow solid foam (1.90 g, 5.48 mmol, 95%).

H. N-(4-Chlorophenyl)-N'-cyanothiourea

The suspension of monosodium cyanamide (1.9 g, 29.4 mmol) in absolute ethanol (5 mL) was slowly treated with 4-chlorophenylisothiocyanate (5.0 g, 29.4 mmol). The reaction was allowed to stir at room temperature for one hour and then heated at 75° C. for four hours. The reaction was cooled to room temperature and the colorless solid was filtered and washed with ethanol to give the title compound (5.4 g), mp>250° C.

I. (3S-trans)-[4-[[[(4-Chlorophenyl)amino](cyanoimino)methyl]amino]-3,4-dihydro-3-hydroxy-2,2-dimethyl-2H-1-benzopyran-6-yl]phenylphosphinic acid, methyl ester To a solution of the title G compound (1.00 g, 2.88 mmol) and the title H compound (762 mg, 3.60 mmol) in 10 mL of anhydrous DMF was added ethyl-3(3-dimethylamino)propylcarbodiimide hydrochloride (828 mg, 4.32 mmol) in one portion at room temperature. The reaction mixture was stirred for 24 hours then partitioned between 50 mL of 10% aq citric add solution and 50 mL of ethyl acetate. The organic layer was separated, washed with 50 mL of water, 50 mL of brine, dried (sodium sulfate) and concentrated in vacuo to give a yellow oil. The crude material was purified by flash chromatography (Merck silica, 20×5.0 cm, 1:2 acetone/methylene chloride) to afford a solid foam. The solid was triturated with ether, collected by filtration and dried under vacuum (60° C.) to give the title compound as a pale yellow solid, (400 mg, 0.76 mmol, 26%) mp 150° (softens).

Analysis calc'd for $C_{26}H_{26}N_4O_4PCl\cdot 0.37H_2O$: C, 58.75; H, 5.07; N, 10.54; Cl, 6.67; P, 5.83. Found: C, 58.79; H, 4.66; N, 10.50; Cl, 6.69; P, 5.63.

EXAMPLE 2

(3S-trans)-N-(4-Chlorophenyl)-N'-cyano-N"-[3,4-dihydro-3-hydroxy-6-(hydroxyphenylphosphinyl)-2,2-dimethyl-2H-1-benzopyran-4-yl]guanidine

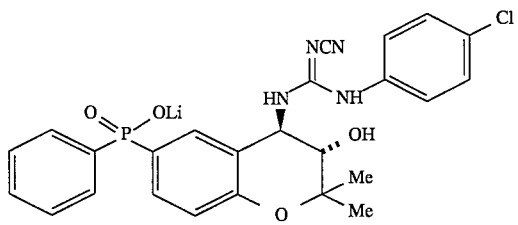

To a solution of the title compound of Example 1 (152 mg, 0.29 mmol) in 1.5 mL of methanol was added 1.5 mL of 1M aq LiOH solution at room temperature. The reaction mixture was stirred for 18 hours (~½ complete by TLC) then an additional 1.5 mL of 1M aq LiOH solution was added. After 18 hours (complete by TLC) the reaction mixture was chromatographed (HP-20, 15×1.5 cm) eluting successively with 100 mL portions of water, 20% aq acetone and 40% aq acetone. The product containing fractions were combined, concentrated in vacuo then lyophilized to afford the title compound as a white solid (165 mg, 0.29 mmol, 100%). $[\alpha]_D=+25°$ (c=0.17 in MeOH).

Analysis calc'd for $C_{25}H_{23}N_4O_4PClLi\cdot 3.02H_2O$: C, 52.57; H, 5.12; N, 9.81; Cl, 6.21; P, 5.42. Found: C, 52.64; H, 5.02; N, 9.74; Cl, 6.52; P, 5.46.

EXAMPLE 3

(3S-trans)-[3,4-Dihydro-3-hydroxy-2,2-dimethyl-4-[[(2-pyridinylamino)carbonyl]amino]-2H-benzopyran-6-yl]-phenylphosphinic acid, methyl ester

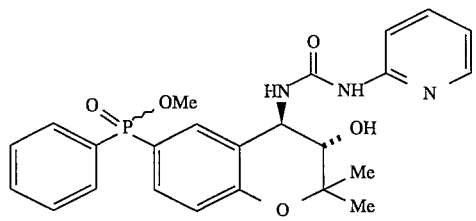

A. 2-Pyridinylcarbamic acid, 4-nitrophenyl ester

A solution of 2-aminopyridine (2.0 g, 21.3 mmol) in methylene chloride (20 mL) was treated with a solution of 4-nitrophenylchloroformate (4.3 g, 21.3 mmol) in methylene chloride (30 mL) followed by the addition of pyridine (1.7 g, 21.3 mmol) under argon. The reaction mixture was allowed to stir at room temperature for 24 hours. The solid was filtered and washed with methylene chloride to give the title compound (4.8 g, 88%) as a light yellow solid.

B. (3S-trans)-[3,4-Dihydro-3-hydroxy-2,2-dimethyl-4-[[(2-pyridinylamino)carbonyl]amino]-2H-benzopyran-6-yl]-phenylphosphinic acid, methyl ester To a solution of the title G compound of Example 1 ((3S-trans)-(4-Amino-3,4-dihydro-3-hydroxy-2,2-dimethyl-2H-1-benzopyran-6-yl)phenylphosphinic acid, methyl ester (300 mg, 0.86 mmol) in 3 mL of anhydrous DMF was added the title A compound (334 mg, 1.29 mmol) at room temperature. The reaction mixture was stirred for 6 h then a second 334 mg portion of the title A compound was added. After an additional 18 h a third 334 mg portion of the title A compound was added. The mixture was stirred for 6 h then diluted with 25 mL of ethyl acetate, washed with three-25 mL portions of 1M aq NaOH solution, dried (sodium sulfate) and concentrated in vacuo to give an oil. The crude oil was purified by flash chromatography (Merck silica, 18×3.0 cm, 1:14 methanol/methylene chloride) to afford the title compound as a solid white foam (128 mg, 0.27 mmol, 32%).

Analysis calcd for $C_{24}H_{26}N_3O_5P \cdot 1.0H_2O$: C, 59.38; H, 5.81; N, 8.66. Found: C, 59.04; H, 5.39; N, 8.78.

What is claimed is:

1. A compound of the formula

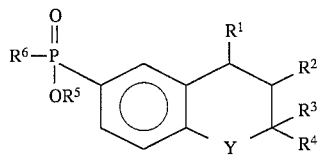

where $R^1$ is

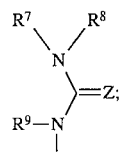

$R^2$ is hydroxy;

$R^3$ and $R^4$ are each independently hydrogen or alkyl;

$R^5$ is alkyl;

$R^6$ is aryl;

$R^7$ is aryl or heterocyclo;

$R^8$ is hydrogen;

$R^9$ is hydrogen;

Y is —O—; and

Z is NCN or O.

2. The compounds as recited in claim 1 wherein

Y is oxygen;

Z is oxygen or NCN;

$R^1$ is

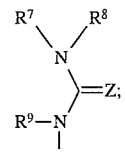

$R^2$ is hydroxyl;

$R^3$ and $R^4$ are methyl groups;

$R^7$ is aryl; and $R^8$ and $R^9$ are hydrogens.

3. The compounds as recited in claim 1, which are:

(3S-trans)-[4-[[[(4-Chlorophenyl)amino](cyanoimino)methyl]amino]-3,4-dihydro-3-hydroxy-2,2-dimethyl-2H-1-benzopyran-6-yl]phenylphosphinic acid, methyl ester;

(3S-trans)-N-(4-Chlorophenyl)-N'-cyano-N"-[3,4-dihydro-3-hydroxy-6-(hydroxyphenylphosphinyl)-2,2-dimethyl-2H-1-benzopyran-4-yl]guanidine; and (3S-trans)-[3,4-Dihydro-3-hydroxy-2,2-dimethyl-4-[[(2-pyridinylamino)carbonyl]amino]-2H-benzopyran-6-yl]-phenylphosphinic acid, methyl ester; or pharmaceutically acceptable salts thereof.

4. A pharmaceutical composition comprising a compound of claim 1 and a pharmaceutically acceptable carrier.

5. A method for treating ischemia comprising administering to a mammalian specie in need thereof a therapeutically effective amount of a composition of claim 4.

* * * * *